United States Patent
Mienie

(12) 
(10) Patent No.: US 6,491,911 B1
(45) Date of Patent: Dec. 10, 2002

(54) BIOLOGICAL AGENT AND METHODS FOR INHIBITING PLANT PATHOGENS

(76) Inventor: Nicolaas Johannes Jacobus Mienie, 393 Kaberoe Avenue, Magalieskruin, Pretoria (ZA), 0150

( * ) Notice: Subject to any disclaimer, the term of this patent is extended or adjusted under 35 U.S.C. 154(b) by 0 days.

(21) Appl. No.: 09/719,474

(22) PCT Filed: Jun. 10, 1999

(86) PCT No.: PCT/ZA99/00043

§ 371 (c)(1),
(2), (4) Date: Mar. 5, 2001

(87) PCT Pub. No.: WO99/63830

PCT Pub. Date: Dec. 16, 1999

(30) Foreign Application Priority Data

Jun. 11, 1998 (ZA) ............................................ 97/11144

(51) Int. Cl.[7] .............................................. A01N 63/00
(52) U.S. Cl. ................................ 424/93.47; 435/253.3; 435/252.4; 424/93.3
(58) Field of Search .......................... 435/253.3, 252.4; 424/93.47, 93.3

(56) References Cited

FOREIGN PATENT DOCUMENTS

| EP | 0 808 571 A1 | 11/1997 |
|---|---|---|
| WO | WO 96 39840 | 12/1996 |

OTHER PUBLICATIONS

Xu et al., Phytophathology, 76:414–422.*
Rosales et al., J. of Phytophathology, 1993, vol. 138, pp. 189–208.*

Moore, Edward R. B. et al.: "The determination and comparison of the 16S rRNA gene sequences of species of the genus Pseudomonas (sensu stricto) and estimation of the natural intrageneric relationships", *Syst. Appl. Microbiol.* (1996), 19(4), 478–492.

Ciampi–Panno, L. et al.: "Biological control of bacterial wilt of potatoes caused by *Pseudomonas solanacearum*", *American Potato Journal*, May 1989, vol. 66, No. 5, p. 315–332.

Berg, G. et al.: "Bacterial antagonists to verticillium dahliae kleb", *Journal of Phytopathology—Phytopathologische Zeitschrift*, vol. 141, Jan. 1, 1994, pp. 99–110.

Yang, C. –H. et al.: "Mutations affecting hyphal colonization and pyoverdine production in pseudomonads antagonistic toward *Phytophthora parasitica*", *Applied and Environmental Microbiology*, (1994) vol. 60, No. 2 (pp. 473–481).

Aoki, Michiko et al.: "Large–scale culture and preservation methods of *Pseudomonas cepacia* B5 for biological control against bacterial wilt disease", *Biosci., Biotechnol., Biochem.* (1993), 57(4), 668–9.

Vaccaneyt, Marc et al.: "Grouping of Pseudomonads by SDS–Page of Whole–cell Proteins", *System and Appl. Microbiol.*, vol. 19, No. 4, 1996, pp. 556–568.

Central–Grass: "An anti–plant pathogenic fungi bacterium and control of plant fungal diseases", *Biotechabs–No. 1998–01013*, Sep. 30, 1997, Abstract of JP–09255513.

* cited by examiner

*Primary Examiner*—Irene Marx
(74) *Attorney, Agent, or Firm*—Popovich & Wiles, P.A.

(57) ABSTRACT

A biological agent and methods for inhibiting plant pathogens are provided. More particularly, this invention provides the use of *Pseudomonas resinovorans* in the biological control of inter alia: Ralstonia solanacearum, Verticillium dahliae and Phytophthora infestans. This invention further relates to a biological combination agent for inibiting *Colletotrichum coccodes*, in addition to the above pathogens.

17 Claims, No Drawings

BIOLOGICAL AGENT AND METHODS FOR INHIBITING PLANT PATHOGENS

INTRODUCTION AND BACKGROUND TO THE INVENTION

1. Field of the invention

This invention relates to a biological agent and methods for inhibiting plant pathogens. More particularly, this invention relates to the use of *Pseudomonas resinovorans* (*R. resinovorans*) in the biological control of inter alia: *Ralstonia solanacearum* (*R. solanacearum*), *Verticillium dahliae* (*V. dahliae*) and *Phytophthora infestans* (*P. infestans*). This invention further relates to a biological combination agent for inhibiting *Colletotrichum coccodes*, in addition to the above pathogens.

For the purposes of this specification, a bacterium is deemed to be characterised by the bacterium deposited at the Centraalbureau voor Schimmelcultures under deposit number 100189, if there is a similarity of more than 85% between the other bacterium and the deposited bacterium, according to the BIOLOG identification system, of Biolog, Inc, 3938 Trust Way, Hayward, Calif. 94545, USA.

2. Description of the Prior Art

*R. solanacearum* (previously known as *Pseudomonas solanacearum*) is a soil-borne, pathogenic bacterium which causes bacterial wilt in plants and which is of substantial economic importance because it is endemic in most if not all the tropical and subtropical countries of the world. *R. solanacearum* colonises the roots of plants and penetrates the xylem and multiply within the vascular tissue of plants. Furthermore, it has a wide host range and the measures for controlling the disease are still limited.

Although some control measures for the biological control of *R. solanacearum* have been developed in vitro, a disadvantage of these measures is that they often fail in vivo and are seldom successful under natural conditions on a commercial scale. These biological control measures often fail under field conditions, because they are mainly based on the assumption that the biological agent is capable of competing with the pathogen under conditions that favour the pathogen, such as naturally infested soils. Reference is made, for example, to Trigalet, A., Frey, P. and Trigalet-Demery, D. 1994. Biological control of bacterial wilt caused by *P. solanacearum*: State of the art and understanding. In: *Bacterial Wilt: The Disease and its causative agent, P. solanacearum* (A. C. Hayward and G. L. Hartman, eds). CAB International pp. 225–233.

U.S. Pat. No. 4,663,162 discloses a method for inhibiting Verticillium wilt on a susceptible host plant, said method including the steps of applying to the host plant an effective amount of *Bacillus polymyxa* 9A, which has been designated A.T.C.C. accession number 39564.

A disadvantage of the said method disclosed in the above patent is that it is not effective against *R. solanacearum*.

*P. resinovorans* has previously been isolated from maize root exudate. However, the antagonistic properties of *P. resinovorans* to *R. solanacearum*, *V. Dahliae*, and *P. infestans* have hitherto been unknown. The applicant has surprisingly found that *P. resinovorans* exhibits antagonistic properties to not only *R. solanacearum*, but also to *V. dahliae* and *P. infestans* and is able to compete with these pathogens in field conditions and on a commercial scale.

OBJECTS OF THE INVENTION

It is accordingly objects of the present invention to provide a biological agent and methods for the inhibition of plant pathogens, with which the aforesaid disadvantages may be overcome or at least minimised and to provide a useful alternative to the known agents and methods.

SUMMARY OF THE INVENTION

According to a first aspect of the invention there is provided a biological agent for inhibiting pathogens in susceptible plants and/or plant material including a bacterium characterised by a bacterium deposited at the Centraalbureau voor Schimmelcultures under deposit number 100189.

Further according to the invention the biological agent includes a bacterium that is of the strain deposited at the Centraalbureau voor Schimmelcultures under deposit number 100189.

Even further according to the invention the agent is effective in the biological control of any one or more of the pathogens selected from the group comprising *Ralstonia solanacearum*, *Verticillium dahliae* and *Phytophthora infestans*.

The biological agent may include another antagonist to pathogens of Solanaceae plants.

The said other antagonist may comprise one or more antagonists selected from the group comprising *Bacillus subtilis* and *Trichoderma harzianum*.

Preferably the other antagonist is non-pathogenic to plants of the family Solanaceae.

Further according to the invention the biological agent includes a carrier for the said bacterium.

The carrier may comprise particulate perlite.

The biological agent may further include a buffer and/or suitable nutrients for the said bacterium.

Preferably the ratio between the said bacterium and the carrier is in the range of between 1:8 to 1:12, on a mass per mass basis.

According to a second aspect of the invention there is provided a method for inhibiting pathogens in susceptible plants and/or plant material including the step of applying the above biological agent to such plants and/or plant material.

According to a third aspect of the invention there is provided a method for inhibiting pathogens in plants and/or plant material including the step of treating said plants and/or plant material with a bacterium characterised by a bacterium deposited at the Centraalbureau voor Schimmelcultures under deposit number 100189.

Further according to the invention the plants and/or plant material are treated with a bacterium that is of the strain deposited at the Centraalbureau voor Schimmelcultures under deposit number 100189.

Even further according to the invention the method is effective in the biological control of any one or more of the pathogens selected from the group comprising *Ralstonia solanacearum*, *Verticillium dahliae* and *Phytophthora infestans*.

The method may include the further step of immobilising the said bacterium in a carrier comprising particulate perlite, a buffer, and nutrients.

The plant material may comprise a potato seed piece and the seed piece may be treated by applying the said bacterium as an aqueous suspension, prior to planting the seed piece. deposited at the Centraalbureau voor Schimmelcultures under deposit number 100189; and *Bacillus subtilis*.

The biological combination agent may further include *Trichoderma harzianum*.

DESCRIPTION OF PREFERRED EMBODIMENTS OF THE INVENTION

Non-limiting examples of preferred embodiments of the invention will now be described by way of example only.

*P. resinovorans* is provided for the treatment of plants and/or plant material to inhibit pathogens, and more particularly to inhibit: Ralstonia solanacearum (R. solanacearum), Verticillium dahliae (V. dahliae) and Phytophthora infestans (P. infestans). P. resinovorans is not toxic and non-pathogenic to plants in general and particularly plants of the family Solanaceae. P. resinovorans was isolated as described below and a sample thereof was deposited on Oct. 30, 1997 at the Centraalbureau voor Schimmelcultures P O Box 273, 3740 AG Baarn, The Netherlands, under accession number 100189.

Alternatively the said seed piece may be treated by applying the said bacterium in the form of a powder, prior to planting the seed piece.

The method may include the further step of applying another antagonist to pathogens of Solanaceae plants.

The said other antagonist may comprise one or more antagonists selected from the group comprising *Bacillus subtilis* and *Trichoderma harzianum*.

According to a fourth aspect of the invention there is provided use of a bacterium characterised by a bacterium deposited at the Centraalbureau voor Schimmelcultures under deposit number 100189, in the manufacture of a biological agent for inhibiting any one or more of the pathogens selected from the group comprising *Ralstonia solanacearum*, *Verticillium dahliae* and *Phytophthora infestans*, in susceptible plants and/or plant material.

According to a fifth aspect of the invention there is provided a biological combination agent for inhibiting any one or more of the pathogens selected from the group comprising *Ralstonia solanacearum*, *Verticillium dahliae*, *Phytophthora infestans*, and *Colletotrichum coccodes* in susceptible plants and/or plant material, the agent comprising a bacterium of the strain The strain was isolated from a maize root exudate and a biological agent containing the isolate was prepared. It was demonstrated that, in potato plants, the agent inhibits disease caused by *R. solanacearum*, *V. dahliae* and *P. infestans*. The agent is suitable for use with a variety of horticultural crops of the family Solanaceae such as tomatoes, potatoes, tobacco and peppers, for example.

The agent is particularly effective for the prevention and/or treatment of *R. solanacearum* Biovar 2 in potato plants and Biovar 3 in tomato plants.

A combination biological agent is further provided comprising a combination of *P. resinovorans* with other antagonists namely *Bacillus subtilis* (*B. subtilis*) and *Trichoderma harzianum* (*T. harzianum*). These additional antagonists were demonstrated to have a synergistic effect with *P. resinovorans*, in that that Solanaceae plants treated with such combination agent thrived vigorously. The combination agent is effective against a broad spectrum of pathogens of plants in the family Solanaceae, including *Colletotrichum coccodes*.

*B. subtilis* and *T. harzianum* are both well known organisms and are generally available to the-public. For example, *B. subtilis* is sold under the trade mark Serenade by AgraQuest, Inc., 1105 Kennedy Place, Davis, Calif. 95615, USA. Further for example, *T. harzianum* is sold under the trade mark Binab T by Bio-Innovation AB, Bredholmen, P O Box 56, S-545 02, ALGARAS, Sweden.

Experimental Methods

Isolation and identification of the Antagonists

Initially, the applicant set out to develop a biological control measure for bacterial wilt and to determine whether any of the bacteria present in a maize root exudate could be used as antagonists of the pathogenic bacteria from the species *R. solanacearum*. A plurality of bacteria were isolated from maize root exudates. All the isolated bacteria were tested for antagonistic properties to *R. Solanacearum* Biovar 2. Seven isolates that exhibited antagonistic properties were selected.

The selected antagonists were cultivated in broth for 48 hours at 25° C. on a shaker. The bacteria in suspension were centrifuged for 10 minutes at 8000 rpm. The pellets that formed were collected and mixed with a 2% alginate mixture. A plurality of potato seed pieces were first dipped in the alginate mixture and directly thereafter submerged in a 0.1M $CaCl_2$ solution. The alginate mixture gelled immediately after being submerged and thus immobilised the antagonists on the surface of the seed pieces. Twenty coated seed pieces per selected antagonist were planted in a green house and after reaching ±15 cm in height, they were inoculated with a *R. solanacearum* suspension comprising $2\times10^6$ cells/ml. The plants were monitored for bacterial wilt and the results are depicted below in table 1.

TABLE 1

[Bar chart: % Survival of Plants vs ANTAGONIST (1-7)]

As is evident from table 1, it was found that only antagonists numbers 1, 3 and 5 exhibited significant antagonistic properties to *R. solanacearum* Biovar 2. The antagonists were identified by using the BIOLOG identification system which showed that:

isolate number 1 was *Sporasarcina urea;* isolate number 3 was *Stenotrophomonas maltophilia;* and isolate number 5 was *Pseudomonas resinovorans.*

Comparative Effectivity of Antagonists

Two different immobilisation matrixes or carriers were used to determine the effectivity of the three selected antagonists against *R. solanacearum* Biovar 2. The antagonist isolates numbers 1, 3 and 5 were cultivated separately on agar plates for 48 hours at 25° C. The antagonists were collected from the agar, divided and a half portion of each antagonist mixed with 2% alginate, which were then dripped in a 0.1M $CaCl_2$ solution, so that the antagonists were immobilised in alginate gel beads. The alginate beads which formed for each antagonist were mixed with peat and placed in 20 separate pots, so that each pot contained 10 g of alginate spheres. A potato seed piece was planted in each pot.

The other half portions of the antagonists were mixed with and immobilised in sterilised peat and placed in 20 separate pots. A potato seed piece was planted in each pot. After the plants had reached a height of ±15 cm, they were each inoculated with a *R. solanacearum* Biovar 2 suspension comprising $2 \times 10^6$ cell/ml. A mixture of all three antagonists was also prepared and the same procedure described above for the individual antagonists was also followed with the mixture. The plants were monitored for bacterial wilt and the results are depicted below in table 2.

TABLE 2

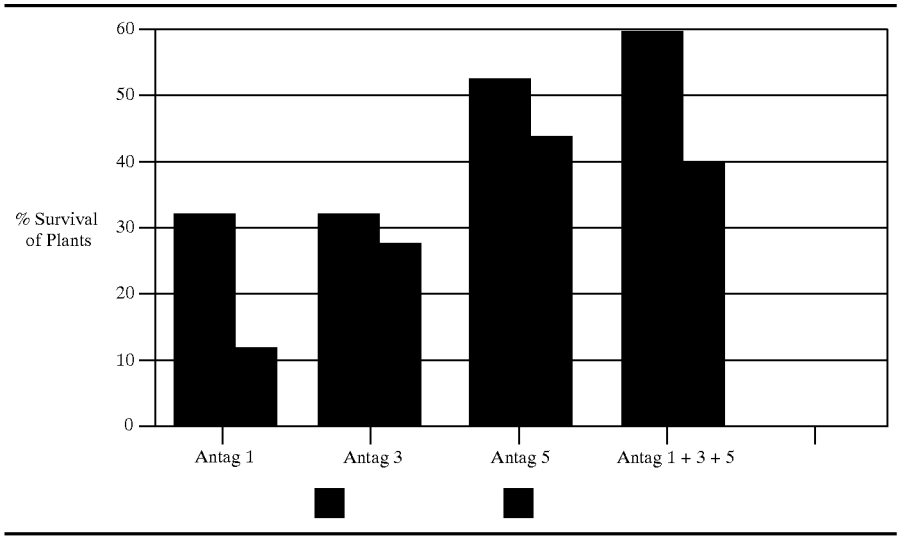

It was found that peat was a more effective carrier than alginate. For example, with antagonist number 1; 32% of the plants survived in the case of peat, compared to 12% in the case of alginate. In the case of antagonist number 3; 32% survived in the case of peat, against 28% in the case of alginate. In the case of antagonist number 5; 52% survived in the case of peat, in comparison with 44% in the case of alginate.

Surprisingly, when a mixture of the antagonists were applied, in the case of peat; 60% of the plants survived after 4 weeks, against only 40% in the case of alginate. 20% more plants thus survived in the case of peat than in the case of alginate.

Some of the advantages of peat as an immobilisation matrix or carder are that it is readily available, relatively cheap in comparison with alginate and environmentally friendly.

It is known that S. maltophilia has pathogenic characteristics (see Krieg, N. R. and Holt, J. G. 1984. Gram-Negative aerobic rods and cocci. In: "Bergey's Manual of Systematic Bacteriology. Williams and Wilkins Baltimore, London.1: 185–186"). S. maltophilia is thus not suitable for use in biological control of bacterial wilt and was discarded.

Although S. urea showed good in vitro inhibition of R. solanacearum, it showed poor results in vivo. S. urea was thus also discarded and further tests were conducted with the P. resinovorans isolates.

Biological Control of Bacterial Wilt

Bacterial-wilt-free, tested, potato seed pieces of the Baroc cultivar were planted separately in pots in soil that was artificially inoculated with *R. Solanacearum*. After 4 weeks, 200 of the plants which grew from the seed pieces were inoculated with 10 ml pure maize root exudate (absorbency 0.01 measured at 620 nm) in the soil, near the base of the stem of each plant and another 200 plants with the *P. resinovorans* antagonist 10 uninoculated control plants per treatment were included. The plants were kept in a greenhouse at 30/22° C. day/night temperature and watered (50 ml per plant) each day with distilled water. The plants were evaluated for wilt symptoms, 40 days after inoculation and scored by using the following disease scale:

0=no wilting symptoms;

1=wilting of one leaf;

2=wilting of up to 50% of the leaves;

3=wilting of all the leaves; and

4=plant dead.

The results were transformed to percentage values (Kremer & Unterstenhöfer, 1967) by using the following formula:

$$P=\sum\frac{(n\times v)}{Z\times N}\times\frac{100}{1}$$

in which

P=percentage of wilting;

n=number of plants in the disease scale (category);

v=numerical value of the disease scale;

Z=highest numerical value of the disease scale; and

N=total number of plants.

The transformed results are depicted below in table 3.

TABLE 3

| Treatment | % Survival of Plant | % Progeny seed pieces infected with *R. solanacearum* | Ave.mass (g) of progeny seed pieces/ pot | % yield in comparison with Control |
|---|---|---|---|---|
| Pure maize root exudate | 12 | 92 | 12.11 | 13.55 |
| Antagonist (*P. resinovorans*) | 68 | 18 | 45.71 | 51.14 |
| Control | 100 | 0 | 89.37 | |

The progeny seed pieces of each of the inoculated plants that survived were tested individually for the presence of the pathogen. The progeny seed pieces were carefully removed from the pots and a sample of 10% progeny seed pieces of each treatment was washed for 3 minutes under tap water, to remove excess soil. The progeny seed pieces were surface sterilized in 1% sodium hypochlorite for 10 minutes and then washed three times in sterile water. Each batch of progeny seed pieces were blended aseptically in 20 ml sterile water in a Waring blender and the suspension used for dilution series. The series were plated on tetrazolium medium (TZC) (Kelma, 1954) agar plates and incubated at 30° C. for 48 hours. Plates were visually examined for typical *R. solonacearum* colonies. Typical colonies were isolated and identified as *R. solanacearum* Biovar 2.

From the above, the following conclusions may be made:

In the case of plants treated with the antagonist; 56% more survived than in the case of plants treated with pure maize root exudate;

74% more of the progeny seed pieces treated with maize root exudate were latently infected with *R. solanacearum* than the antagonist treated seed pieces; and The seed pieces treated with the antagonist had approximately 38% higher yield in progeny seed pieces than in the case of pure maize root exudate.

Systemic Absorption of Antagonist

It was furthermore determined whether the antagonist *P. resinovorans* was absorbed systemically by the potato plants. In vitro plants of the potato cultivar Baroc were prepared on Osborne medium. The plants were cultivated on the medium until they reached a height of approximately 5 cm. *P. resinovorans* was cultivated on nutrient agar and incubated at 30° C. for 24 hours. After incubation, the inoculum was prepared to have a final concentration of $10^6$ cfu's/ml. 5 ml of the inoculum was placed in a sterile tube and the in vitro plants removed aseptically from the tube and placed in the inoculum, such that only the root zone was submerged in the inoculum. The tube was sealed aseptically and incubated at 30° C. for 24 hours.

After the incubation period, the plants were removed aseptically from the inoculum and the root zone cut off and the plants surface-sterilised with NaOCl. The roots were placed on agar plates and incubated for 48 hours. The leaves and stem of the plant were removed and the stem cut in 3 mm portions from the stem base to the grow point. The seed pieces were numbered in sequence and placed on agar plates and incubated for 48 hours.

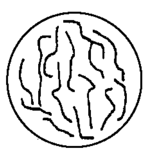

REPRESENTATION A

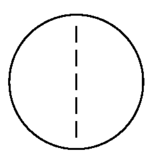

REPRESENTATION B

After the incubation period, the antagonist grew out of the roots as is shown in representation A and it was clear that the antagonist was absorbed by the roots of the plant and had established itself in the endo-rhizosphere of the plant. The antagonist also grew out of each piece of stem, from the base to the grow point, as is clear from representation B. It was thus clear that the antagonist was absorbed systemically by the vascular tissue of the plant.

Development of a Combination Agent

Subsequently, the experimentation was extended to determine whether *P. resinovorans* could be used in conjunction with other antagonists in a biological combination agent for inhibiting a broad spectrum of pathogens. For this purpose, *B. subtilis* and *T. harzianum* were selected. The antagonistic properties of these organisms against *P. resinovorans* and against each other were tested in vitro. The selected antagonists were tested on agar plates by using the cross-streaking technique. The plates were incubated for seventy-two hours and the results are depicted in table 5.

TABLE 5

| ANTAGONIST | *P. resinovorans* | *B. subtilis* | *T. harzianum* |
|---|---|---|---|
| *B. subtilis* | No inhibition | | No inhibition |
| *T. harzianum* | No inhibition | No inhibition | |

Discussion

The results demonstrated that there was no inhibition between and the other antagonists, and between the antagonists themselves.

Spectrum of the Combination Agent

The experiments were further extended to determine whether the *P. resinovorans* and *B. subtilis* are effective against other well-known pathogens of plants in the family Solanaceae. These two organisms were evaluated against *Colletotrichum coccodes, Phythophthora infestans* and *Verticillium dahliae* for in vitro inhibition, using the cross-streaking technique on NA plates. The results are depicted below in table 6.

TABLE 6

| Candidate antagonists | *Colletotrichum coccodes* | *Phythophthora infestans* | *Verticillium dahliae* |
|---|---|---|---|
| *B. subtilis* | Total inhibition | Total inhibition | Total inhibition |
| *P. resinovorans* | Partial inhibition | Total inhibition | Total inhibition |

Discussion

*B. subtilis* showed total inhibition of *Colletotrichum coccodes, Phythophthora infestans* and *Verticillium dahliae.* This tendency showed the potential for the use of this bacterium as an additional antagonist in the combination agent. *P. resinovorans* showed total inhibition of *Phythophthora infestans* and *Verticillium dahliae,* but partial inhibition of *Colletotrichum coccodes.* No experiments were conducted with *T. harzianum* in this regards, but it is known that *T. harzianum* is an antagonist against a wide range of pathogenic fungi, and for that reason it was also included in the combination agent.

Systemic Uptake of Combination Agent

In order to determine whether the antagonists of the combination agent were taken up systemically by potato plants and whether the isolates colonised the endo-rhizosphere of the plants, the same procedure that is described above for *P. resinovorans,* was conducted with the combination agent. The results of the procedure are depicted below in table 7.

TABLE 7

| | Was the organism taken up systemically? | Did the organism colonise the endo-rhizosphere? | Did the organism colonise the exo-rhizosphere? |
|---|---|---|---|
| *P. resinovorans* | Y | Y | Y |
| *B. subtilis* | Y | Y | Y |
| *T. harzianum* | N | N | Y |

Discussion

Both *B. subtilis* and *P. resinovorans* were taken up systemically and colonised both the endo- and exo-rhizospheres. *T. harzianum* was not taken up systemically but did colonise the exo-rhizosphere.

Selection of Suitable Carrier for Field Trial

Over and above the alginate and peat carriers referred to above, other carriers in which the agent could be immobilised, were further investigated. One particular carrier showed promising results in field trials, namely the carrier disclosed in South African Patent number 96/6318, filed in the name of Helga Dagutat and entitled "MICROBIAL CARRIER AND INOCULUM". This carrier comprises a fine particulate, inorganic, silicious mineral such as perlite, with a silicon dioxide concentration of between 60 and 90% by weight. The mineral also contains aluminium, sodium and potassium, with traces of iron, calcium, magnesium, manganese and titanium. This carrier is henceforth simply referred to as the carrier.

Field Trials Conducted with *P. resinovorans* (Isolate Number CBS100189)

Subsequently, the applicant extended its research to determine the effectiveness of *P. resinovorans* (CBS100189) as a biological agent for the inhibition of pathogens, under field conditions.

The following agents were prepared, namely
Agent 1—1 g *P. resinovorans* (CBS100189) inoculated in 10 g perlite carrier in powder form;
Agent 2—1 g *P. resinovorans* (CBS100189) inoculated in 30 g carrier;
Agent 3—7,5 g G10 inoculated in 7,5 g carrier (G10 is a mixture of non-pathogenic growth promoting bacteria that does not include any particular antagonists.); and
Control—30 g carrier with no antagonists.

The agents and the control were each applied in dry powder form to 30 potato seed pieces respectively. The treated seed pieces were planted in infected soil and the progeny plants investigated. The results are set out in below in table 8.

TABLE 8

|  | % Plants suffering from wilt 10 weeks after emergence | % ring symptoms in progeny plants 10 weeks after emergence |
| --- | --- | --- |
| Agent 1 | 12 | 2 |
| Agent 2 | 10 | 6 |
| Agent 3 | 92 | 54 |
| Control | 98 | 60 |

Discussion

From the above it is clear that *P. resinovorans* (100189) inhibited wilt disease in the treated plants, in field conditions. In comparison to the control, agent 1 caused a 68% reduction in wilt disease in the plants, 10 weeks after the plants have emerged. Agent 1 further caused a reduction of 85% of ring symptoms in comparison to the control. Agent 2 showed similar results as agent 1 and it was clear that an increase in the amount of carrier did not make any significant difference. A preferred ratio between the antagonist and the carrier is in the range of 1:8 to 1:12, on a mass per mass basis.

As expected, agent 3 compared with the control due to the fact that no antagonist was included.

Field Trials Conducted on a Commercial Scale

Subsequently trials were conducted to determine the effectiveness of *P. resinovorans* (100189), under field conditions on a commercial scale. 120 bags of the agent were prepared, with each bag comprising a mixture of 20 ml *P. resinovorans* (100189) suspension and 210 g of the perlite carrier described above, in dry powder form. The experiment was carried out as follows:

Control—39 seed pieces coated with the perlite carrier in dry powder form planted in pathogen infected soil;
Batch 1—39 seed pieces planted in pathogen infested soil treated with a solution of 10 bags of the agent in sterile water;
Batch 2—39 seed pieces planted in pathogen infested soil treated with a solution of 20 bags of the agent in sterile water;
Batch 3—39 seed pieces planted in pathogen infested soil treated with a solution of 30 bags of the agent in sterile water;
Batch 4—39 seed pieces coated with the agent in dry powder form and planted in pathogen infested soil;

The seed pieces of batches 1–3 were also submerged in the agent solution prior to planting. The treated seed pieces of the control and the batches were respectively planted in 3 rows of 13 seed pieces each in pathogen infested soil. The plants were investigated 10 weeks after emergence for ring symptoms. The results are depicted below in table 9.

TABLE 9

|  | % Ring symptom free tubers (Medium) | % Ring symptom free tubers (Large) |
| --- | --- | --- |
| Control | 90.62 | 50.40 |
| Batch 1 | 98.73 | 97.80 |
| Batch 2 | 99.10 | 98.17 |
| Batch 3 | 99.64 | 99.50 |
| Batch 4 | 99.60 | 100 |

Discussion

From the above results it is clear that *P. resinovorans* (100189) is highly suitable for use in a biological control agent on a commercial scale, particularly when applied in dry powder form. Furthermore, the use of *P. resinovorans*, either on its own or in conjunction with other antagonists, as an endophytic antagonistic biological agent for the inhibition of pathogens, has several advantages over the use of a surface antagonist. For instance, once the antagonist has established itself within the plant, it persists as the plant develops and thereby provide continuous protection. *P. resinovorans* (100189) has the further advantages that it has no known pathogenic characteristics and that it is able to compete with pathogens under natural conditions on a commercial scale. *P. resinovorans* has the following characteristics:

Rods, 0.6–0.7×2.0–2.5 $\mu$m. Motile by means of a polar flagellum. Fluorescent pigment is produced. Gelatin is not liquefied. Nitrate reduction is weak, and denitrification is negative. Oxidase reaction positive. Optimum growth temperature, 28/30° C.; no growth at 5° C. or 42° C. No acid is produced from arabinose, xylose, rhamnose, glucose, fructose, galactose, mannose, lactose, maltose, sucrose, raffinose, inulin, salicin, dextrin, glycerol, mannitol, inositol or dulcitol. Starch hydrolysis very weak. Growth occurs at the expense of colophony, Canada balsam or abietic acid. Phenol, phenanthrene, salicylic acid, m-cresol and naphthalene can also be used as carbon and energy sources for growth.

It will be appreciated that many variations in detail are possible with a biological agent and methods according to the invention without departing from the scope and/or spirit of the appended claims.

What is claimed is:

1. A biological agent for inhibiting pathogens in plant material susceptible to pathogen infection comprising a biologically pure culture of the *Pseudomonas resinovorans* strain deposited at the Centraalbureau voor Schimmelcultures, P.O. Box 273, 3740 AG Baarn, the Netherlands, on Oct. 30, 1997, under accession number 100189.

2. The biological agent according to claim 1 wherein said biological agent is effective in the biological control of *Ralstonia solanacearum*.

3. The biological agent according to claim 1, further comprising an antagonist to pathogens of Solanaceae plants, said antagonist being selected from the group consisting of *Bacillus subtilis* and *Trichoderma harzianum*.

4. The biological agent according to claim 3 wherein said antagonist is non-pathogenic to plants of the family Solanaceae.

5. The biological agent according to claim 1, further comprising a carrier for said *Pseudomonas resinovorans*.

6. The biological agent according to claim 5 wherein said carrier comprises particulate perlite.

7. The biological agent according to claim 6 wherein said biological agent further comprises a buffer.

8. The biological agent according to claim 6 wherein said biological agent further comprises nutrients.

9. The biological agent according to claim 5 wherein the ratio between the *Pseudomonas resinovorans* and the carrier is between about 1:8 to about 1:12, on a mass per mass basis.

10. A method for inhibiting pathogens in plant material susceptible to pathogen infection comprising: (a) providing at least one plant material; (b) providing a carrier; (c) inoculating said carrier with a viable culture of the *Pseudomonas resinovorans* strain deposited at the Centraalbureau voor Schimmelcultures, P.O. Box 273, 3740 AG Baarn, the Netherlands, on Oct. 30, 1997, under accession number 100189; and (d) coating said plant material with the inoculated carrier.

11. A method for inhibiting pathogens in plant material susceptible to pathogen infection comprising: (a) providing at least one plant material; and (b) treating said at least one plant material with a viable culture of the *Pseudomonas resinovorans* strain deposited at the Centraalbureau voor Schimmelcultures, P.O. Box 273, 3740 AG Baarn, the Netherlands, on Oct. 30, 1997, under accession number 100189.

12. The method according to claim 11, said method being effective in the biological control of *Ralstonia solanacearum*.

13. The method according to claim 11 further comprising a step of immobilizing said *Pseudomonas resinovorans* in a carrier comprising particulate perlite, a buffer, and nutrients.

14. The method according to claim 11 wherein said at least one plant material comprises a potato tuber and wherein the method further comprises: (c) applying an aqueous suspension of said *Pseudomonas resinovorans* onto said tuber; and (d) planting said tuber.

15. The method according to claim 11 wherein said plant material comprises a potato tuber and the method further comprises: (c) applying said *Pseudomonas resinovorans* as a powder form onto said tuber; and (d) planting said tuber.

16. The method according to claim 11 further comprising a step of applying an antagonist to pathogens of Solanaceae plants, said antagonist being selected from the group consisting of *Bacillus subtilis* and *Trichoderma harzianum*.

17. A method of manufacturing a biological agent for inhibiting *Ralstonia solanacearum* in plant material comprising: (a) providing a carrier; and (b) inoculating the carrier with a viable culture of the *Pseudomonas resinovorans* strain deposited at the Centraalbureau voor Schimmelcultures, P.O. Box 273, 3740 AG Baarn, the Netherlands, on Oct. 30, 1997, under accession number 100189.

* * * * *